(12) United States Patent
Liang et al.

(10) Patent No.: US 11,041,820 B1
(45) Date of Patent: Jun. 22, 2021

(54) MAGNETIC HOLDER FOR IMMUNOELECTRON MICROSCOPY GRIDS

(71) Applicant: Institute of Microbiology, Chinese Academy of Sciences, Beijing (CN)

(72) Inventors: Jingnan Liang, Beijing (CN); Yiwei Liu, Beijing (CN); Qian Wang, Beijing (CN); Zhousinuo Jiang, Beijing (CN); Xing Dai, Beijing (CN); Hao Liang, Beijing (CN); Yuanming Luo, Beijing (CN); Chunli Li, Beijing (CN); Zheng Fan, Beijing (CN); Tong Zhao, Beijing (CN); Shutao Sun, Beijing (CN); Xiaolan Zhang, Beijing (CN)

(73) Assignee: Institute of Microbiology, Chinese Academy of Sciences, Beijing (CN)

( * ) Notice: Subject to any disclaimer, the term of this patent is extended or adjusted under 35 U.S.C. 154(b) by 0 days.

(21) Appl. No.: 17/140,043

(22) Filed: Jan. 2, 2021

(30) Foreign Application Priority Data

Jan. 7, 2020 (CN) .......................... 202010015283.2

(51) Int. Cl.
*G01N 23/2202* (2018.01)
*G01N 23/2204* (2018.01)
*G01N 33/532* (2006.01)
*G01N 1/28* (2006.01)

(52) U.S. Cl.
CPC .......... *G01N 23/2202* (2013.01); *G01N 1/28* (2013.01); *G01N 23/2204* (2013.01); *G01N 33/532* (2013.01); *G01N 2223/309* (2013.01); *G01N 2223/612* (2013.01)

(58) Field of Classification Search
None
See application file for complete search history.

(56) References Cited

U.S. PATENT DOCUMENTS

2014/0169533 A1 * 6/2014 Razzano ................ A61B 6/587
378/205
2020/0297133 A1 * 9/2020 Huffar .................. G06Q 20/208

* cited by examiner

*Primary Examiner* — Hoon K Song
(74) *Attorney, Agent, or Firm* — Zhu Lehnhoff LLP

(57) ABSTRACT

The present invention relates to a magnetic holder for immunoelectron microscopy grids. The holder comprises a frame, a magnet and a hydrophobic layer. The device can use a magnetic force to simultaneously attach the outer rings of nickel grids to the frame, so that a batch operation (such as rinsing, immunolabeling and dyeing) of the nickel grids can be realized. In addition, due to the hydrophobic effect of the hydrophobic layer, the holder can reduce the amount of the liquid carried by the nickel grids in the process of continuously transferring the nickel grids between different types of liquids to almost zero. Compared with the prior art, the magnetic holder effectively reduces the probability of cross-contamination between reagents.

13 Claims, 4 Drawing Sheets

MAGNETIC HOLDER FOR IMMUNOELECTRON MICROSCOPY GRIDS

This application claims the priority of Chinese Patent Application No. 202010015283.2, filed on Jan. 7, 2020, the entire disclosure of which is incorporated herein by reference.

TECHNICAL FIELD

The present invention relates to a holder for carrying nickel grids with biological ultrasections used in immunoelectron microscope sample preparation technology, in particular to a holder for carrying the nickel grids with a high throughput during rinsing, antigen-antibody labeling and staining.

BACKGROUND ART

A nickel grid is a necessary ultrasections carrier applied to biological sample preparation technology of immunoelectron microscope. The nickel grid comprises two parts: one is a nickel ring with a rim width of about 0.2 mm, and another is hollow grids of different sizes ranging from 50-200 meshes inside the nickel ring. The thickness of the whole nickel grid is about 18 micrometers. There is an organic Formvar layer on the front of the nickel grid. Some laboratories spray a carbon membrane of few nanometers thickness on the outer surface of the Formvar membrane which is used to reduce the non-specific adsorption capacity of immune colloidal gold and to provide stronger support for sections. The immunolabeling operation of biological samples is performed on the nickel grid. The entire operation comprises many steps such as rinsing (multiple times), blocking liquid incubation, primary antibody incubation, rinsing (multiple times), secondary antibody incubation, rinsing (multiple times), fixative, rinsing (multiple times), and staining. Usually the transfer of the nickel grid in each step of the operation is realized by using a pair of tweezers to grip the nickel ring with a rim width of about 0.2 mm around the nickel grid. If the tweezers touch the grid inner area of the nickel grid in this process, the tweezers can easily touch sections on the grid or the Formvar membrane or carbon membrane adheres to the surfaces of the grids, thereby directly or indirectly damaging the sections loading on the nickel grid, thus affecting following observation. In addition, in the process of transferring the nickel grid, there is often residual liquid that was not cleaned in the previous step in the gap of the tweezers and carried into the next reaction solution, which can easily lead to section contamination (i.e. unexpected background) Under high-resolution observation of an electron microscope, these unexpected background are irregularly mixed with the secondary antibody colloidal gold particles of only 6-15 nm in the immunolabeling, which seriously affects the imaging effect. Furthermore, usually one immunolabeling experiment needs to simultaneously process multiple sets of sections for labeling under different test conditions; and the number of sections processed in batches is large. This multiplies the steps of transferring sections, the error rate, and the operation time.

In order to achieve the unification of the stain time of each section, there is a device for copper grids batch staining in the prior art. CN105910875A discloses a device which can perform batch staining on the copper grids. The device comprises a main body for fixing the copper grids with sample sections and an auxiliary body for fixing and supporting the main body. The main body comprises soft layers and a hard layer covered by the soft layers, wherein the cross section of the hard layer is arc-shaped or angle-shaped. The copper grid is fixed in the device by the soft layers at the two sides of an arc-shaped opening or an angle-shaped opening.

The above device is mainly used for the copper grid. The copper grid has a high hardness and can be easily inserted into a wax layer; but a nickel grid has a low hardness, and is difficult to insert it into a wax layer. In addition, the device is only suitable for a single staining operation. If the device is used to load a batch of copper grids and continuously transfer the grids in liquid of multiple steps, it will carry too much residual liquid from the previous steps.

SUMMARY OF THE INVENTION

A main technical problem solved by the present invention is to provide a device that can be used for batch operation (such as rinsing, immunolabeling, dyeing, etc.) on nickel grids and can reduce the amount of residual liquid carried by the nickel grids in the process of continuously transferring the nickel grids in liquid of multiple steps.

In order to solve the above technical problem, the present invention provides a magnetic holder for immunoelectron microscopy grids, comprising a frame, magnets and a hydrophobic layer As a preferred structure of the present invention, the frame comprises at least one arm made of a solid material, the arm has a hollow interior and axisymmetric arc-shaped grooves located at an upper end and a lower end of an outer surface of the arm and close to the hollow interior, the magnets are detachably arranged below the frame, and the hydrophobic layer adheres to the outer surface of the magnetic holder.

As a preferred structure of the present invention, the frame comprises at least two arms made of a solid material, the frame further comprises a connecting part, each of the arms has a hollow interior, the magnets are disposed in the hollow interiors of the arms, the connecting part is used for connecting the arms, and the hydrophobic layer adheres to an outer surface of the magnetic holder.

The beneficial technical effects of the present invention: the uniform transfer of batches of sample-loaded nickel grids in different reaction solutions is realized. Through the present invention, not only can the reaction time of the section in each of the sample-loaded nickel grids be unified, but also greatly reduce the mechanical damage to the grids, and it can also reduce the amount of liquid carried out by nickel grids during the continuous replacement of the nickel net between different liquids to almost zero, which greatly improves the success rate of immunolabeling at the sample preparation level.

BRIEF DESCRIPTION OF THE DRAWINGS

The accompanying drawings are used to provide a further understanding of the present invention and constitute a part of the specification. The drawings are used to explain the present invention together with the following exemplar examples, but do not constitute a limitation to the present application. In the drawings.

DETAILED DESCRIPTION OF THE INVENTION

The specific embodiments of the present invention will be described in further detail below in conjunction with the drawings and embodiments. The following examples are used to illustrate the present invention, but not to limit the scope of the present invention.

Example 1

Figure 1:
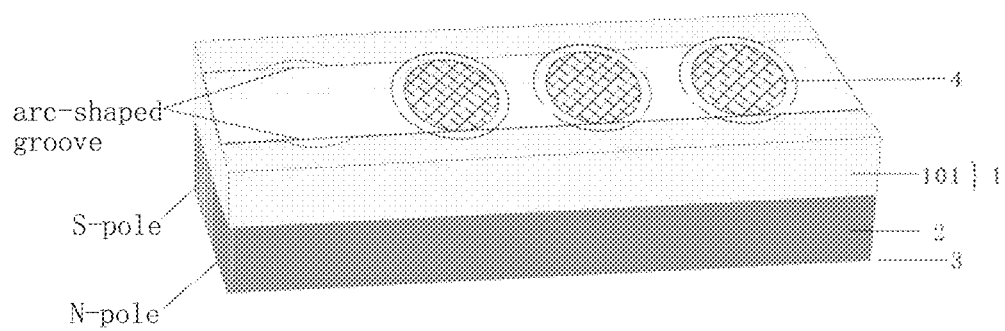
FIG. 1 is a schematic diagram of a magnetic holder with a frame located at one side of a magnet.
Figure 4:
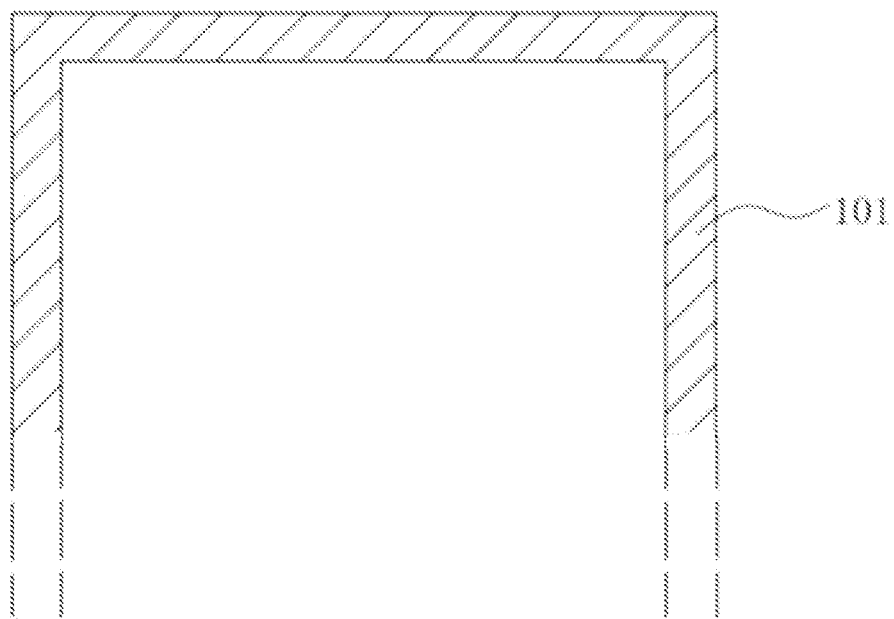
FIG. 4 is a schematic transverse cross-sectional view of one of the arms of the frame of FIG. 1.

As shown in FIG. 1, a magnetic holder for nickel grids with a frame located entirely at one side of a magnet comprises the frame 1, the magnet 2 and a hydrophobic layer 3. The frame 1 comprises at least one arm 101 with a hollow interior (shown in FIG. 4). The arms 101 are made of a solid material. The distance between these hollow interiors of the arms is 2.6 mm. A plurality of axisymmetric arc-shaped grooves are provided in positions located at an upper end and a lower end of an outer surface of the arms 101 and close to the hollow interiors. The openings of the arc-shaped grooves all face the opposite sides, and the two symmetrical arc-shaped grooves can just accommodate the nickel ring on the outside of one nickel grid. The magnet 2 is a magnetic iron detachably arranged below the frame 1. The hydrophobic layer 3 adheres to the outer surfaces of the frame 1 and the magnet 2.

Operation: separating the frame 1 and the magnet 2, placing the outer rings of the upper sides and lower sides of the plurality of nickel grids 4 respectively in the symmetrical arc-shaped grooves of the arms 101, recombining the frame 1 loaded the nickel grids 4 and the magnet 2, and carrying out the immunolabeling operation. After the immunolabeling is completed, separating the frame 1 and the magnet 2 again. Finally taking out the nickel grids 4. The nickel grids 4 are fixed by the magnetic force of the magnet 2 under the frame 1 to achieve the batch staining for the nickel grids 4. The nickel grids 4 can be prevented from carrying too much residual liquid in the process of transferring between different reaction liquids by the hydrophobic effect of the hydrophobic layer. By separating the frame 1 from the magnet 2, it is possible to avoid the interference of the magnetic force on the nickel grids when the nickel grids are put into the frame or taken out of the frame.

Example 2

Figure 2:
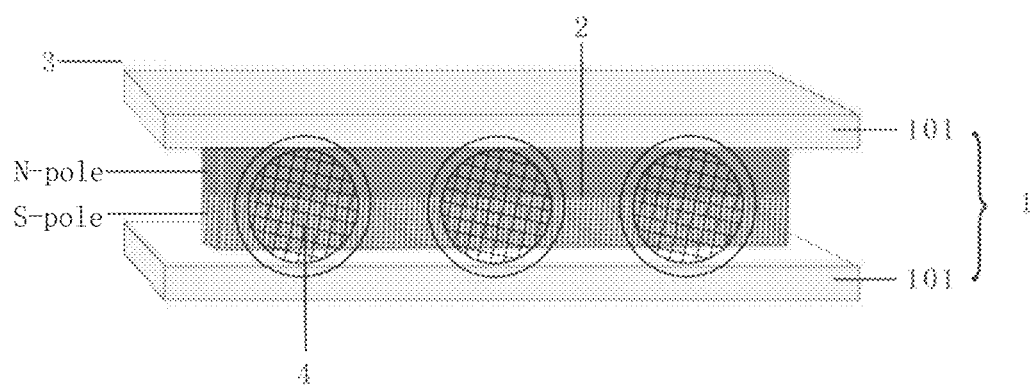
FIG. 2 is a schematic diagram of a magnetic holder with a magnet located between two adjacent arms.

As shown in FIG. 2, a magnetic holder for immunoelectron microscopy grids with a magnet located between two adjacent arms comprises a frame 1, the magnet 2 and a hydrophobic layer 3. The frame 1 comprises at least two axisymmetric arms 101. The distance between the two adjacent arms 101 is 2.6 mm to 3 mm. The thickness of one arm 101 is not less than 0.1 mm. Each of the arms 101 is made of a solid material such as iron, cobalt or nickel, which are easily magnetizable. The hydrophobic layer 3 adheres to the outer surface of each of the arms 101. The magnet 2 is a magnetic iron with a length and a width being both smaller than that of the arms 101. The magnet 2 is located between the two adjacent arms 101, and connects and magnetizes the arms 101. The hydrophobic layer 3 adheres to the outer surface of the magnet 2.

Operation: placing the outer rings of the upper sides and lower sides of the plurality of nickel grids 4 correspondingly on the two adjacent arms 101 magnetized by the magnet 2. The nickel grids 4 are fixed by the magnetic force of the arms 101 so as to achieve the batch immunolabeling operation of the nickel grids 4. The nickel grids 4 can be prevented from carrying too much residual liquid in the process of transferring between different reaction liquids by the hydrophobic effect of the hydrophobic layer.

Example 3

Figure 3:
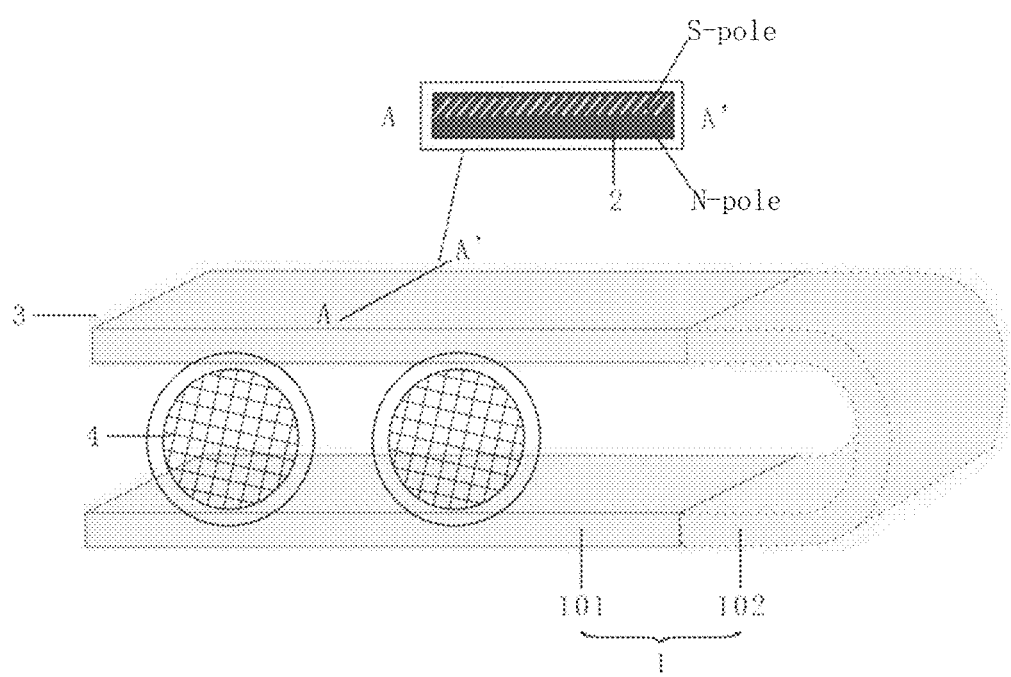
FIG. 3 is a schematic diagram of a magnetic holder with magnets located inside arms, showing a A-A' cross section.

As shown in FIG. 3, a magnetic holder for immunoelectron microscopy grids with magnets located inside arms comprises a frame 1, the magnets 2 and a hydrophobic layer 3. The frame 1 comprises at least two axisymmetric arms 101 and a connecting part 102. The overall thickness of one arm 101 is not less than 0.1 mm. The interiors of the arms are hollow, and the exteriors of the arms are made of a solid material. The arms 101 are connected by the connecting part 102. The distance between the two adjacent arms 101 is 2.6 to 3.3 mm. The magnets 2 are magnet iron located in the hollow interiors of the arms 101. The hydrophobic layer 3 adheres to the outer surface of the frame 1.

Operation: placing the outer rings of the upper sides and lower sides of the plurality of nickel grids 4 correspondingly on the two adjacent arms 101. The nickel grids 4 are fixed by the magnetic force of the magnetic bodies inside the arms 101 so as to achieve the batch immunolabeling operation of the nickel grids 4. The nickel grids 4 can be prevented from carrying too much residual liquid in the process of transferring between different reaction liquids by the hydrophobic effect of the hydrophobic layer.

The invention claimed is:

1. A magnetic holder for nickel grids for use in immunoelectron microscopy, comprising a frame, a first magnet a hydrophobic layer adhered to an outer surface of the holder, and a plurality of nickel grids fixed to a surface of the frame by the first magnet, each nickel grid having a nickel ring and a mesh grid disposed inside the nickel ring.

2. A holder as claimed in claim 1 wherein:
   each nickel ring has an inner diameter and an outer diameter:
   the frame comprises first and second arms opposing each other and spaced from each other by a gap which is smaller than the outer diameter of the nickel rings and which is greater than or equal to the inner diameter of the nickel rings;
   the first magnet contacts the frame and generates a magnetic force through the frame which fixes the nickels grids to the frame with the nickel ring of each nickel grid spanning the gap between the two arms of the frame.

3. A holder as claimed in claim 2 wherein each arm has a flat surface adjoining the gap for supporting the nickel rings of the nickel grids fixed to the frame by the first magnet.

4. A holder as claimed in claim 2 wherein the hydrophobic layer adheres to the first magnet.

5. A holder as claimed in claim 2 wherein:
   each arm of the frame has a plurality of arc-shaped grooves formed along the gap in an upper surface of the arm and spaced from each other in a lengthwise direction of the arm, each groove having an opening which faces the opposing arm, each groove being axisymmetric with respect to one of the grooves in the opposing arm, each groove accommodating a portion of the periphery of the nickel ring of one of the nickel grads spanning the gap between the arms.

6. A holder as claimed in claim 5 wherein each groove extends partway through a depth of the arm in which the groove is formed.

7. A holder as claimed in claim 5 wherein the first magnet is detachably arranged below and in contact with the arms of the frame.

8. A holder as claimed in claim 2 wherein:
the first magnet is located in the gap between the two arms and connects and magnetizes the arms and generates a magnetic force which fixes the nickel grids to the frame with the nickel grids spanning the gap.

9. A holder as claimed in claim 8 wherein each arm has a length and a width, and the first magnet has a length which is smaller than the length of either arm and a width measured in a widthwise direction of the frame which is smaller than the width of either arm.

10. A holder as claimed in claim 8 wherein each arm is made of a magnetizable material.

11. A holder as claimed in claim 2 further comprising a second magnet and a connecting member which extends between and connects the first and second arms, wherein the first magnet is disposed in a hollow interior of the first arm and the second magnet is disposed in a hollow interior of the second arm, and the first and second magnets generate magnetic forces which fix the nickel grids to the frame with the nickel grids spanning the gap between the arms.

12. A holder as claimed in claim 11 wherein the first arm surrounds a periphery of the first magnet and the second arm surrounds a periphery of the second magnet.

13. A holder as claimed in claim 11 wherein the connecting member is connected to a lengthwise end of each arm.

* * * * *